United States Patent [19]

Tsang et al.

[11] Patent Number: 5,088,833
[45] Date of Patent: Feb. 18, 1992

[54] METHOD AND APPARATUS FOR MONITORING CLOUD POINT OR LIKE TRANSITION TEMPERATURE

[75] Inventors: Charles Y. Tsang; Victoria S. Ker, both of Calgary, Canada

[73] Assignee: Nova Husky Research Corporation, Calgary, Canada

[21] Appl. No.: 454,270

[22] Filed: Dec. 21, 1989

Related U.S. Application Data

[63] Continuation-in-part of Ser. No. 307,502, Feb. 8, 1989, abandoned.

[30] Foreign Application Priority Data

Feb. 10, 1988 [CA] Canada ................... 558566

[51] Int. Cl.⁵ ..................... G01N 25/04; G01N 25/12
[52] U.S. Cl. ..................... 374/17; 374/20; 374/27
[58] Field of Search ........... 374/17, 18, 19, 20, 374/16, 27, 28; 73/29, 335; 356/446; 340/601, 602; 364/550, 556, 557

[56] References Cited

U.S. PATENT DOCUMENTS

| | | | |
|---|---|---|---|
| 3,077,764 | 2/1963 | Kapff | 374/19 |
| 3,112,648 | 12/1963 | Dulk et al. | 374/19 |
| 3,187,557 | 6/1965 | Holbourne | 374/19 |
| 3,248,928 | 5/1966 | Conklin et al. | 374/19 |
| 3,269,185 | 8/1966 | Francisco | 374/19 |
| 3,447,358 | 6/1969 | Crespin et al. | 374/16 |
| 3,457,772 | 7/1969 | Chassagne et al. | 374/17 |
| 3,527,082 | 9/1970 | Pruvot et al. | 374/17 |
| 3,528,278 | 9/1970 | Sterling | 374/19 |
| 3,545,254 | 2/1971 | Chassagne et al. | 374/17 |
| 3,580,047 | 5/1971 | Simpson | 374/22 |
| 3,581,554 | 6/1971 | LaFitte et al. | 374/19 |
| 3,623,356 | 11/1971 | Bisberg | 374/20 |
| 3,643,492 | 2/1972 | Simpson | 374/23 |
| 3,807,865 | 4/1974 | Gordon et al. | 374/17 |
| 4,083,224 | 4/1978 | Gayst | 374/19 |
| 4,276,768 | 7/1981 | Dadachanji | 374/28 |
| 4,519,717 | 5/1985 | Jones | 374/27 |
| 4,629,333 | 12/1986 | Dosoretz et al. | 374/45 |
| 4,799,235 | 1/1989 | Bannell et al. | 374/18 |
| 4,826,327 | 5/1989 | Michell | 374/20 |

FOREIGN PATENT DOCUMENTS

| | | | |
|---|---|---|---|
| 638309 | 4/1964 | Belgium | 374/28 |
| 1299437 | 7/1969 | Fed. Rep. of Germany | 374/18 |
| 3247689 | 6/1984 | Fed. Rep. of Germany | 374/18 |
| 645069 | 1/1979 | U.S.S.R. | 374/28 |
| 851221 | 7/1981 | U.S.S.R. | 374/16 |
| 1276976 | 12/1986 | U.S.S.R. | 374/28 |
| 1438754 | 6/1976 | United Kingdom | |
| 2036339 | 6/1980 | United Kingdom | 374/19 |
| 2043242 | 10/1980 | United Kingdom | 73/29 |
| 2202941 | 10/1988 | United Kingdom | 374/16 |

OTHER PUBLICATIONS

Series 1200 Dew Point Hygrometer (Apr. 1979).
"Electronic Hygrometer Senses Dew Point Precisely", Product Engineering, pp. 79-80 (Mar. 1968).
Gralenski, F. M., "Automatic Dewpoint Hydrometer", Instr. & Control Systems, vol. 37, pp. 124-125 (May 1964).

*Primary Examiner*—William A. Cuchlinski, Jr.
*Assistant Examiner*—Diego F. F. Gutierrez
*Attorney, Agent, or Firm*—Rothwell, Figg, Ernst & Kurz

[57] ABSTRACT

Apparatus for monitoring the cloud point of a liquid, or the temperature at which any light scattering phase occurs therein, comprising a light-proof and light-absorbing chamber, and a liquid sample-receiving receptacle within the chamber having a bottom formed by a non-light-scattering surface; this surface being in thermal contact with a heating or cooling device, such as a thermoelectric cooler, and with a temperature measurement device. The chamber can be opened to allow access to the receptacle so that sample liquid can be placed therein. A light beam source is located to direct a beam of light onto the surface at an incident angle so that light from the beam is reflected or absorbed by the surface. A light detector including a lens and an array of detection cells is arranged so as to detect scattered light which is produced when solid material forms in the liquid as it is cooled or disappears on heating. The melting point of a solid, or the boiling point of a liquid, can be detected, in additoin to cloud points.

18 Claims, 6 Drawing Sheets

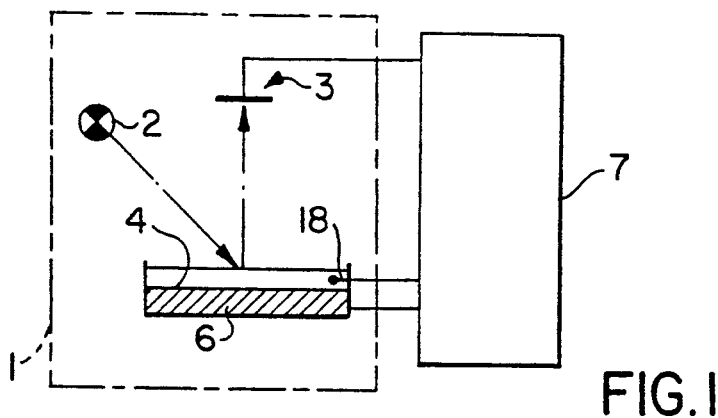
FIG. 1
FIG. 2a
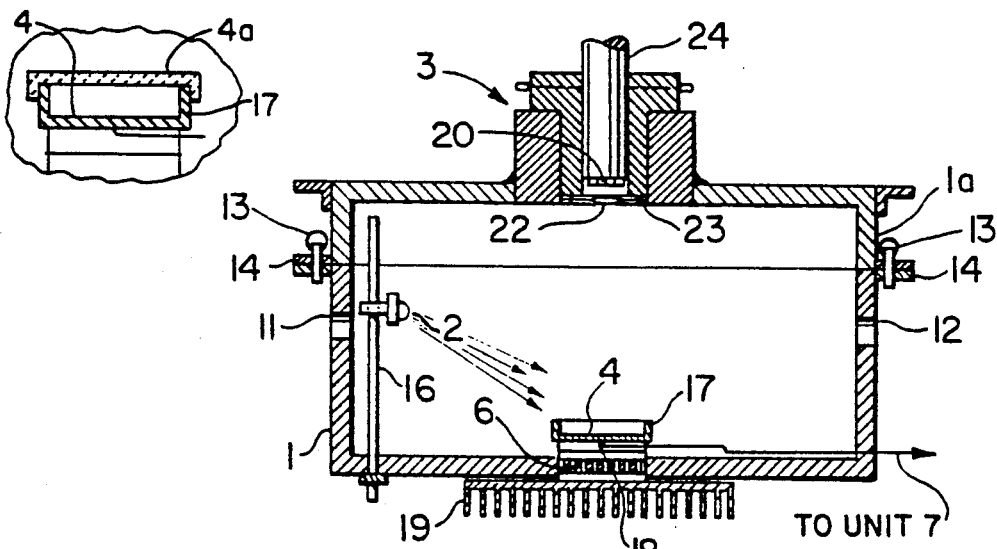
FIG. 2
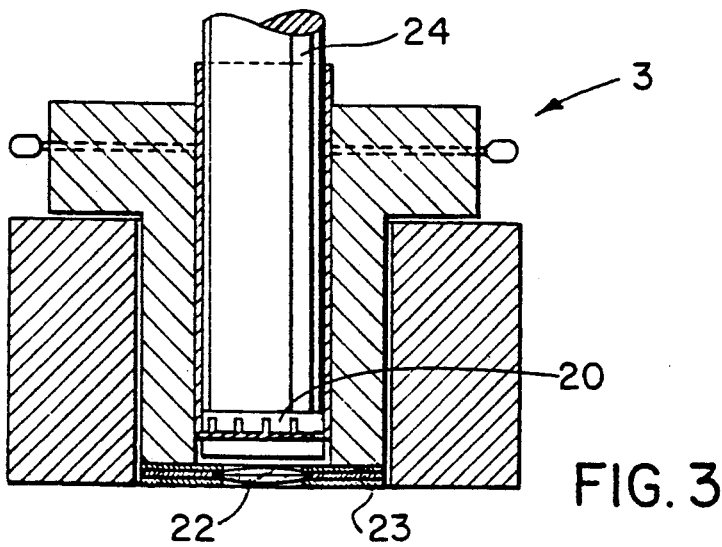
FIG. 3

METHOD AND APPARATUS FOR MONITORING CLOUD POINT OR LIKE TRANSITION TEMPERATURE

CROSS REFERENCE TO RELATED APPLICATIONS

This application is a continuation-in-part of pending U.S. application Ser. No. 307,502, filed Feb. 8, 1989, now abandoned.

FIELD OF INVENTION

This invention relates primarily to the measurement of the cloud point of petroleum oils. It may also apply to the measurement of the temperature at which a transition occurs between any transparent or translucent liquid which is non-light scattering, and a light scattering phase. Such transitions include the formation of a light scatttering phase which may be a solid, immiscible liquid, or gas phase in a liquid, and also include the disappearance of a light scattering phase as in the measurement of the melting point of a solid. In all cases however a transparent non-light scattering liquid phase is present, unlike when light scattering droplets of liquid condense from a gas.

BACKGROUND AND PRIOR ART

The cloud point of petroleum oil, as defined by the American Society of Testing and Materials (ASTM) standard method D-2500, is the temperature at which haziness caused by formation of small crystals is first observed in a sample of oil which is cooled under prescribed conditions. The method requires that the sample be cooled in a series of constant temperature baths until the cloud point appears. The temperature of each bath, and the temperature at which the sample is transferred from one bath to the next one of lower temperature, are specified in the method.

The cooling rate of an oil sample treated in the manner described above is cyclical. The rate is highest after the sample is transferred due to the large difference in the temperature between the bath and the oil sample. From then on the cooling rate decreases as a function of time until the next transfer takes place. These different cooling rates give rise to inaccuracies of measurement; the true cloud point should be obtained under slow cooling. The preferred cooling rate for petroleum oils is one degree Centigrade per minute, or less. At cooling rates higher than this value the observed cloud point has a tendency to increase with increasing cooling rate and the precision of measurement deteriorates.

In addition, the current ASTM cloud point method requires a considerable amount of an operator's time to make one determination. An operator's subjective judgement is also required to determine the onset of haziness in the sample.

Since the cloud point method has been established, numerous inventors have come forward with ideas to automate the measurement. Most of the ideas were centred around improvements related to the automatic detection of cloud formation and automatic charging and discharging of a sample cell. These systems tend to be expensive and have various drawbacks.

Thus, many prior art systems require complex and expensive cooling systems either because a large sample of liquid is required or because a fairly large chamber is cooled. Use of a large sample also gives rise to possible inaccuracies caused by lack of temperature uniformity. Such systems are described in:

U.S. Pat. No. 3,077,764 which issued Feb. 19, 1963 to Kapff;

U.S. Pat. No. 3,248,928 which issued May 3, 1966 to Conklin et al;

U.S. Pat. No. 3,527,082 which issued Sept. 8, 1970 to Pruvot et al;

U.S. Pat. No. 3,580,047 which issued May 25, 1971 to Simpson;

U.S. Pat. No. 3,643,492 which issued Feb. 22, 1972 to Simpson;

U.S. Pat. No. 3,447,358 which issued June 3, 1969 to Crespin et al; and

U.K. Patent No. 1,438,754 published June 9, 1976.

Other prior art systems have generally enclosed cells or containers through which the liquid sample is caused to flow. In addition to being relatively complicated, such arrangements may make cleaning of the cell or vessel difficult. Such arrangements are shown in:

U.S. Pat. No. 3,187,557 which issued June 8, 1965 to Holbourne;

U.S. Pat. No. 3,457,772 which issued July 29, 1969 to Chassagne et al;

U.S. Pat. No. 3,545,254 which issued Feb. 13, 1968 to Chassagne et al;

U.S. Pat. No. 4,519,717 which issued May 28, 1985 to Jones et al.

U.S. Pat. No. 3,807,865 (issued Apr. 30, 1974 to Gordon et al.) shows an arrangement in which a small sample of liquid is placed in a glass tube which has previously been sealed at one end, and which is then "drawn off and sealed as close to the upper meniscus of the sample as convenient". The tube is placed in a flowing heat transfer fluid to effect cooling; temperature is measured by a thermometer close to the tube. The presence of a solid phase is detected by monitoring for light scattered when a light beam is passed axially into the tube.

In most of the proposals described in previous patents, the cooling rate of the oil sample was either poorly defined or uncontrolled. For example, U.S. Pat. No. 3,187,557 suggests a quick cooling as it mentions a 60 times decrease in analysis time as compared with the ASTM method. In U.S. Pat. No. 4,519,717, a variable times shorter than the ASTM method. Such high cooling rates have been shown to result in inaccuracy.

It has also been suggested in U.S. Pat. No. 4,083,224 to Gayst (issued Apr. 11, 1978) that apparatus designed for dewpoint measurement might be used for measuring the freezing point of a liquid. This suggestion comes in a short last paragraph of Gayst, and no details are given. Gayst describes a dewpoint monitor in which light reflected off a mirror is monitored by a light detector and a reduction in such reflected light, due to scattering by droplets, is measured. Adopting such apparatus for use in determining freezing point would encounter some problems not addressed by Gayst, e.g.

(1) The reflected light would also be refracted when a liquid is present in the well, altering the light received by the light detector depending on depth of liquid and the refractive index, which will change as the temperature is lowered.

(2) The change in reflected light caused by the cloudiness typical of cloud point measurements would be so small as to be probably undetectable with Gayst's apparatus, especially since his reflected light detector can only "see" a central part of the mirror surface and would not detect crystals near to the side.

(3) Gayst provides no enclosure which would exclude ambient light, another reason why his device would likely be unable to detect small crystals.

(4) Gayst does not have any provision for dealing with a liquid or solid substance requiring a protective atmosphere.

SUMMARY OF THE INVENTION

The invention provides both a method and apparatus primarily intended for the measurement of cloud point, but also suitable for measuring the temperature at which any light scattering phase forms or disappears in a transparent non-light scattering liquid when this is heated or cooled. Such phase may be a solid, an immiscible liquid or a gas. Thus, the invention can be used for measuring the temperature of transitions between miscible and immiscible liquids, of production of a gaseous phase when a liquid boils, and transitions between a solid and liquid at melting or solidification.

According to one aspect of the invention, apparatus for measuring the temperature at which a transition occurs between a transparent or translucent non-light scattering liquid and a light scattering phase comprises:

a generally light proof chamber having lightabsorbing internal surfaces and having a gas inlet;

a liquid sample-receiving receptacle within said chamber and having its bottom formed by a heat conductive material with an upper surface which is non-light scattering;

means allowing ready access to the chamber for placing a sample of liquid in said receptacle and allowing removal of the liquid from the receptacle at the termination of the test;

means in thermal contact with said bottom for changing the temperature of said bottom and means for determining the temperature of said bottom in thermal contact therewith;

a light beam source located to direct a beam of light onto said upper surface at an incident angle so that light from the beam is largely reflected or absorbed by said upper surface; and scattered light detection means arranged so as to detect light scattered by said sample and changes in intensity of the scattered light and connected into circuit means capable of registering a change in light scattered from the said sample as said bottom is heated or cooled, the detection means including a lens which concentrates the light from the sample onto a light detecting element.

In this invention, the receptacle can be quite shallow and has a diameter of about 5 mm to 15 mm. This means that only a small quantity of sample (a few drops) is required, and the receptacle is easily cleaned. Preferably, the depth of liquid is less than 2 mm. The receptacle may be open-topped or have a removable transparent cover.

The upper surface of the receptacle is preferably a smooth horizontal mirror surface. In this case the scattered light is of course measured at a location separated from the light beam reflected from the mirror surface so that the reflected beam does not interfere with scattered light measurements. Preferably, the incident angle between the light beam and the mirror surface is an acute angle of from 20° to 70°, and the scattered light is measured in a direction perpendicular to the surface.

BRIEF DESCRIPTION OF THE DRAWINGS

The invention will be described in more detail with reference to the accompanying drawings, which show a preferred embodiment of the apparatus, and in which:

FIG. 1 is a schematic diagram of the apparatus including associated electrical components;

FIG. 2 is a sectional elevation through the apparatus;

FIG. 2a shows a fragmentary part of FIG. 2 with a modification;

FIG. 3 is a detailed sectional view of the light detector.

FIG. 6: solid—liquid system: freezing point of distilled water;

FIG. 7: solid—liquid system: freezing point of cyclohexane;

FIG. 8: solid—liquid system: freezing point of benzene;

FIG. 9: solid—liquid system: freezing point of sodium chloride solution;

FIG. 10: solid—liquid system: freezing point of 30% antifreeze, 70% water mixture;

FIG. 11: immiscible liquids: 30% triethylamine, 70% water; and

FIG. 12: liquid—gas system: boiling point of N-butane.

DESCRIPTION OF THE PREFERRED EMBODIMENT

Figure 4:
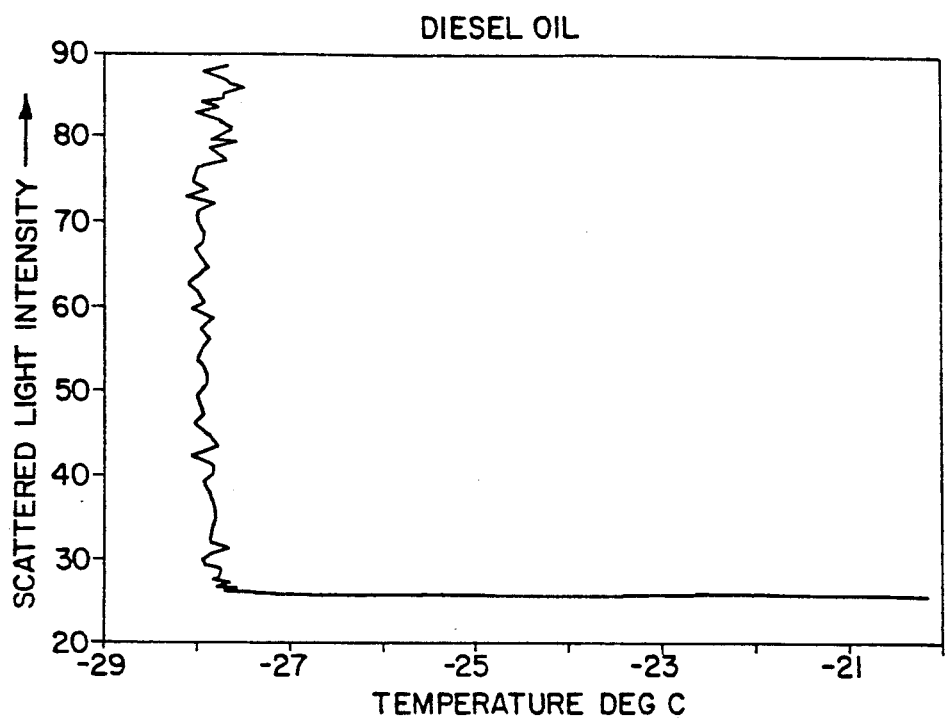
FIG. 4 is a graph showing the changes of scattered light intensity with changes in temperature, obtained using the method and apparatus of this invention, for diesel oil cooled below the cloud point.

The cloud point measurement device shown in FIGS. 1 and 2 consists of a light proof chamber 1, a light source 2, a light detection unit 3, a non-light scattering surface 4 which forms the bottom of a receptacle for a liquid sample, a thermoelectric cooler 6 in thermal contact with the surface 4, and a data acquisition unit and control unit 7 for the device. The thermoelectric cooler can be used both for cooling and for heating.

The chamber 1 is designed to withstand low gas pressure of approximately 5-10 psig., and two gas inlet/outlet ports 11 and 12 located in the lower portion of the chamber allow the chamber to be purged with a dry gas to avoid condensation of water inside the unit. The chamber has a removable top part in the form of a lid portion 1a, held in place by hinges (not shown) and by clamps 13 which engage peripheral flanges 14. It will be noted that the lid portion is readily removable by the release of clamps 13, i.e. is removable without use of tools, and that uppon removal it allows full access to the receptacle from above allowing this to be cleaned and refilled while in its fixed position. The entire inner surface of chamber 1 and all the inner attachments, except for the surface 4, is light absorbing and preferably in black, to prevent reflection of light from these surfaces.

The light source 2 is a light-emitting diode mounted on a ⅛" (3 mm) rod 16 which can be moved in the vertical direction and can also be rotated to allow the best adjustment of incidence angle of the light beam on the surface 4. The angle of incidence between the light beam and the surface 4 is always an acute angle within the range from 20° to 80° and preferably about 45°.

The non-light scattering surface is located at the centre of the cell. In this preferred embodiment, this surface is a highly polished flat mirror 4 forming the top surface of the bottom of a receptacle for the sample. As shown, this is an open topped receptacle having an annular sidewall 17, both the bottom and sidewall being formed integrally of copper. The receptacle is shallow in relation to its width being about 2 mm deep and having an area of about 1 square cm so as to contain a maximum of 0.2 cc of liquid.

The receptacle having mirror 4 is mounted on the top surface of thermoelectric cooler 6 so as to be in good thermal contact therewith, and the temperature of the surface is measured by a platinum resistance thermometer 18 affixed to the bottom part of the mirror and also in good thermal contact therewith. Other suitable temperature measurement devices may be used. The cooler 6 is capable of removing heat from the mirror and delivering it to a heat sink 19.

The light detection unit 3, used to detect scattered light produced at the formation of a light scattering phase, is carried by the lid portion 1a and placed directly above the mirror 4 so to be on a light transmittance path perpendicular to the mirror. This unit, shown in FIG. 3, consists of an array of charge coupled devices (CCD) 20 for detecting the intensity of scattered light, and a convex lens 22 held by 0-ring 23 to concentrate the light onto the CCD array. The CCD array is mounted on a plastic rod 24, movable in the vertical direction. This allows the best adjustment of the CCD for reception of the scattered light through the fixed lens. The sensitivity of the CCD array and the use of a lens allows this to detect the formation of small crystals anywhere in substantially the whole area of the mirror 4.

The data acquisition and control unit 7 is used to collect information from the thermocouple 18 and the CCD 20, to control the cooling rate of the mirror 4 and also to determine the transition temperature such as onset of cloud point. A computer equipped with the necessary software and hardware is utilized for this purpose.

The method of operation, when used for detecting cloud point in a liquid, will now be described with reference to FIG. 4, which shows results obtained in testing a Diesel oil as follows:

Prior to the test, one must ensure that the mirror 4 is clean and dry. The lid portion 1a of the chamber is opened, and liquid sample is introduced into the chamber by using a pipette or dropper to place about 0.1–0.2 mls of liquid onto the mirror 4, followed by closing and clamping the lid. The chamber is then purged slowly with a dried gas for about two minutes and then kept pressurized at a level of 1-2 psi. The temperature of the mirror is lowered by cooler 6 at a predetermined rate, about 0.8° C./min., under the control of unit 7, the light source 2 is activated and the light beam is directed onto the mirror 4. Prior to the formation of cloud in the sample, the light beam is almost entirely reflected, and only a small amount of scattered light is detected by the detection unit 3; this is shown as a generally horizontal line in FIG. 4. Once clouds or wax crystals start to form, the intensity of scattered light increases; FIG. 4 shows that this occurs between −27.5° C. and −28° C. Therefore, by monitoring the light intensity received by the detector unit 3 as a function of temperature, the cloud point of the sample can be determined. At the end of the test, the thermoelectric cooler is switched off to allow the temperature of the mirror to return to ambient. The unit is then depressurized and opened up to allow cleaning of the sample receptacle. Since the light detector is carried by the removale lid the receptacle is easily cleaned while in its fixed position.

As compared to prior art mechanized systems, the present invention has the following advantages:

(1) It requires only small amount of liquid sample; in the embodiment described this is less than 0.2 cc. Preferably the depth is no more than 2 mm. A greater depth might be used but this is expected to be less than 5 mm.

(2) The small amount of cooling capacity required means that a relatively cheap thermoelectric cooler can be used in place of much more expensive conventional refrigeration apparatus. In some instances, such devices may also be used to heat the sample above ambient temperature.

(3) The shallow receptacle is easily cleaned, preventing cross-contamination. Although it contains only a small sample, it is wide enough to allow easy cleaning.

(4) Any lack of uniformity of temperature from top to bottom of the sample does not seriously affect the results. In the cooling mode the bottom of the sample will be coldest, but as soon as any cloud or crystals occur at this point the CCD will register scattered light; the presence of warmer liquid towards the top of the receptacle is of no consequence. Since the temperature measuring device is in thermal contact with the bottom of the receptacle this accurately measures the temperature at which the cloud point occurs.

While a highly polished mirror has been found to give the best results, useful measurements can also be made using a receptacle the bottom surface of which is black and therefore light absorbing, and substantially non light-scattering. Both smooth and rough black surfaces can be used.

The apparatus has been described as using an open-topped receptacle, which is of course the most convenient. However, a receptacle with a transparent lid such as lid 4a shown in FIG. 2a may be used for volatile liquids and to prevent drying during an experimental run.

Figure 5:
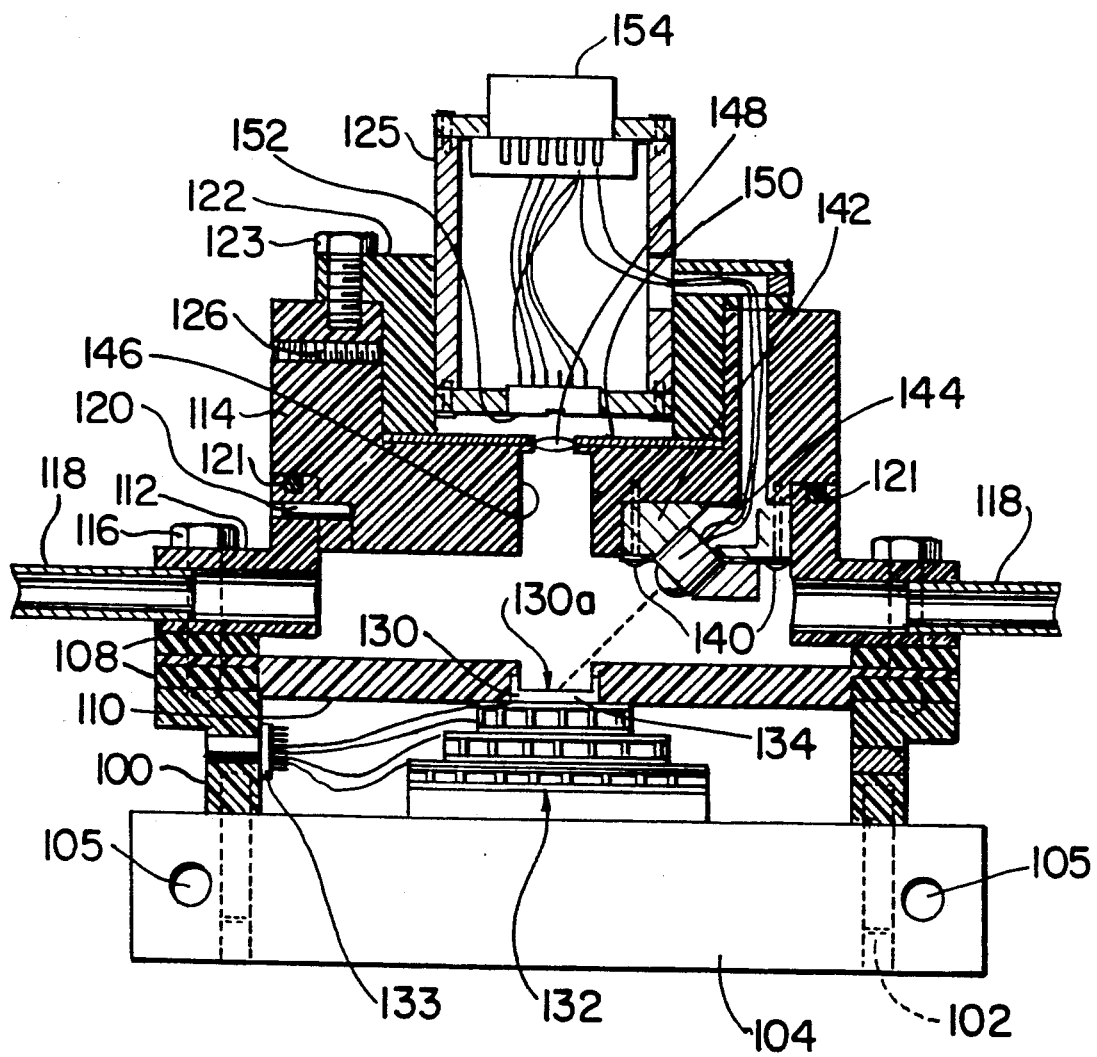
FIG. 5 is a sectional elevation through a modified form of the apparatus of the invention.

FIG. 5 shows a modified form of the apparatus. As shown, an annular base part 100 is mounted by bolts 102 onto a water cooled, metallic heat sink 104 having water ducts 105. The base part supports, via gaskets 108, the horizontal bottom closure 110 of a light excluding chamber having an annular housing 112 with a large central aperture normally closed by a readily removable top part 114. The housing 112 is fixed to bottom closure 110 and base 100 by bolts 116. It has radial ducts connected to gas inlet and outlet tubes 118 so that the chamber can be purged with a non-condensing gas.

The top part 114 is removably secured to housing 112 by a bayonet type coupling, i.e. the kind of two component coupling having radial pins on one component which engage in partially circumferential grooves in another component. Here, the coupling includes radial pins 120 which project inwardly from housing 112 and engage in grooves in the adjacent cylindrical surface of top part 114, the grooves having axial portions allowing entry of the pins and circumferential portions allowing locking. An 0-ring 121 provides a seal between the two parts.

The top part 114 has a cylindrical top recess which slidingly receives a split bushing 122, secured in place by bolts 123. The bushing in turn slidingly receives a cylindrical detector holder 125. A radial screw 126, screw threaded into the side of part 114, can be tightened against the side of bushing 122 to cause this to grip the detector holder 125, allowing this to be vertically adjusted within the bushing and to be secured in place by the screw.

The parts 110, 112, 114 and 122 are all made of black plastic material, so as to be light absorbing and so as to be thermally insulating at least as compared to metal parts. Nylon or ABS plastic may be used.

The centre of the bottom closure 110 has a circular aperture the bottom of which is counterbored to receive a receptacle 130 formed from copper; this fits snugly within the counterbore so that the upper walls of the aperture are continuations of the inner walls of the receptacle. The upper surface 130a of the receptacle bottom is a polished flat mirror of about 10 mm diameter and preferably between 5 mm and 15 mm. The side walls, including the aperture upper walls, are about 4 mm in height above the upper surface 130a, and preferably less than 5 mm, so that the height:diameter ratio of the well formed by the receptacle and side walls is about 1:2. These dimensions are significant in that the receptacle must be readily cleaned in changing over from one material to another.

Between the lower side of the receptacle bottom and the heat sink 104 is firmly held a thermoelectric cooler 132 which is in good heat conductive contact with both the receptacle and the heat sink. These latter items are of course all of heat conductive metal. The cooler is capable of reducing the temperature of the receptacle to $-50°$ C. or lower.

The cooler 132 is spaced well away from the walls of the base 100. The base is provided with a side bore holding a connector 133 for wires which run both to the cooler 132 and to a platinum resistance thermometer 134 in contact with the lower side of the receptacle bottom.

At one side of the underside of top part 114 is a shallow cylindrical recess which holds, by screws 140, a light holder 142 which mounts a light emitting diode 144. This is arranged to direct a beam of light onto the mirror surface 130a, at an angle of approximatley 45°.

Co-axially above the receptacle 130 is a bore 146 in part 114, this bore being of similar diameter to the receptacle and terminating just short of the lower surface of the recess which receives bushing 122, with which recess it communicates via a central aperture. A convex lens 148 has its edges trapped between the periphery of this aperture and the periphery of a similar aperture in a metal plate 150 held between part 114 and bushing 122. The lens concentrates light received from the surface 130a onto light detection means 152 comprising an array of charge coupled devices (CCD). This array has 128 pixels which together receive light from substantially the whole area of surface 130a. With this arrangement a signal is produced as soon as light scattering occurs anywhere in the viewing area, whether this is caused by crystals in a cooling liquid or bubbles in a boiling liquid. The use of the lens makes this arrangement extremely sensitive to small amounts of scattered light, only affecting a few pixels, and provides much greater light sensitivity than a single light detecting cell. Each pixel of the CCD array is separately connected via connector 154 to a data acquisition and monitoring computer which monitors sequentially each of the pixels of the CCD array. The leads from the light emitting diode 144 pass through the same connector.

Operation of the device is similar to that described with reference to the first embodiment. Again, only a small amount of liquid, less than 2 mm in depth, is used; the greater depth of the receptacle is intended to minimize spilling. The computer controls the cooling of mirror surface 130a and processes signals received from the thermometer 134 and from the CCD array 152. The computer monitors the output of each pixel part separately. The computer displays on a monitor screen continuous indications of temperature intervals and of the average intensity of the scattered light received by the pixels of the CCD array as the mirror surface 41 is cooled.

FIGS. 6 to 12 show graphs of other experiments done with various systems with this apparatus.

Figure 6:
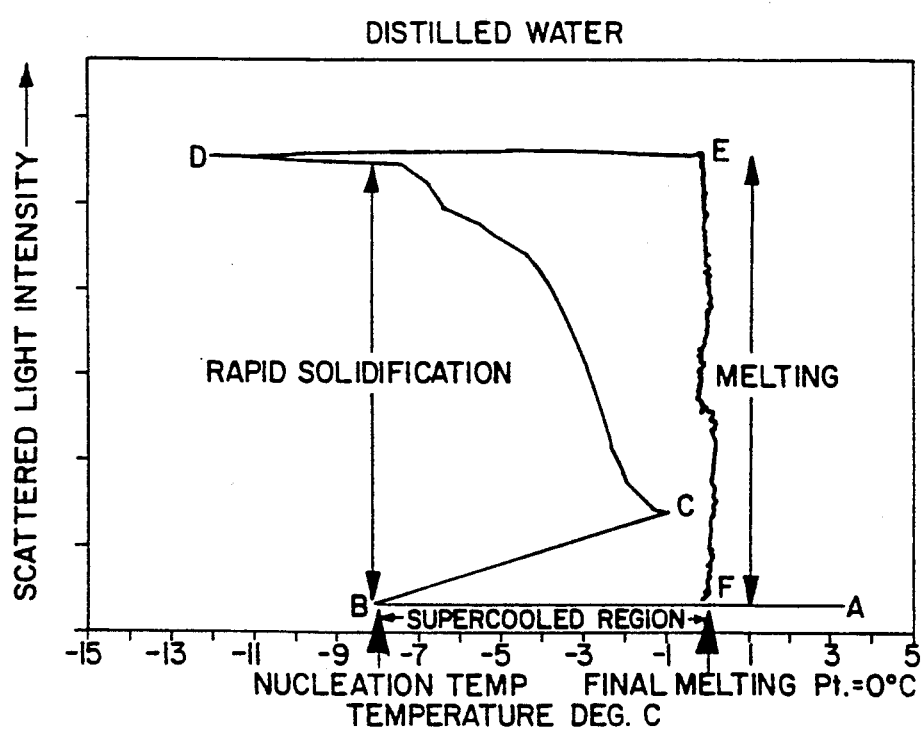
FIGS. 6 to 12 are graphs similar to FIG. 4 for the following systems.

FIG. 6 summarizes the results of an experiment with distilled water. The experiment started at point "A" where the liquid was cooled down slowly. The light scattering intensity did not increase as the temperature passed 0° C. due to supercooling of the liquid. Finally, nucleation of ice occurred at point "B", followed by a rapid crystal growth period and simultaneous release of latent heat. The fast release of latent heat caused the temperature of the system to rise to point "C".

Beyond point "C", the growth of crystals slowed down gradually until the entire sample was solidified at point "D". At that stage, the cooling power of the cooler was reduced and the temperature of the system was allowed to rise. At point "E", where the temperature was 0° C., the scattered light intensity dropped as the melting process began. The sample was close to completely melted at point "F".

Figure 7:
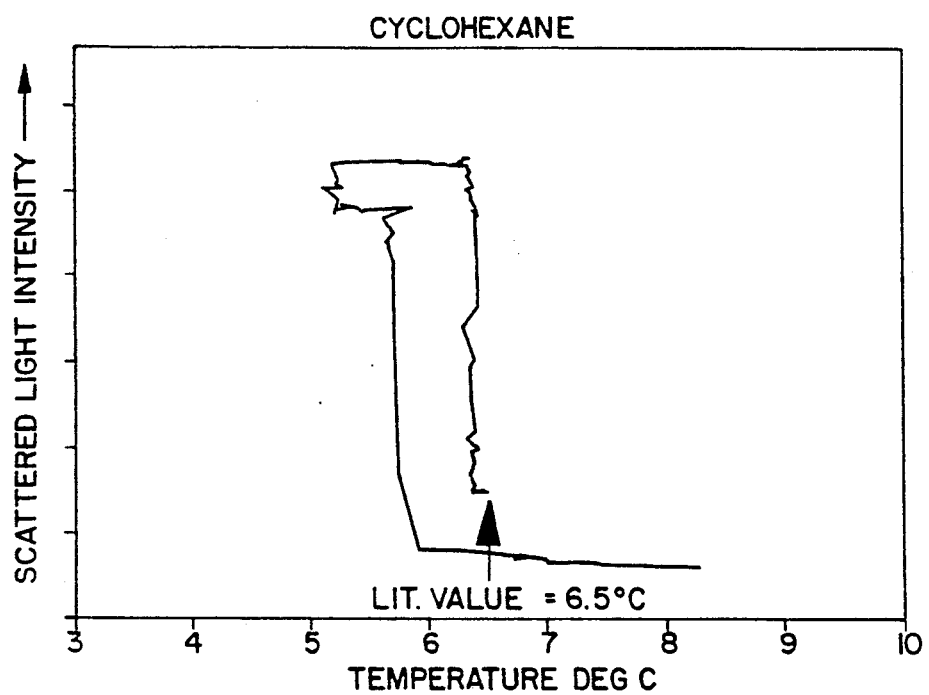
Figure 8:
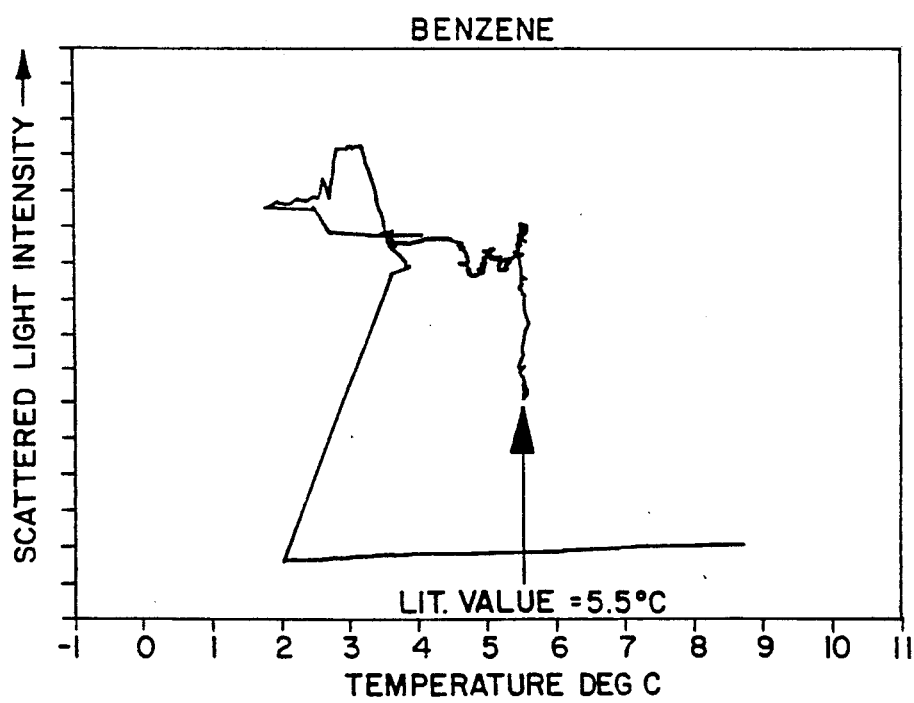

FIGS. 7 and 8 show the results for other pure liquids, respectively cyclohexane and benzene. The melting points determined by the device agreed well with those reported in the literature as shown on the graphs. In FIG. 7, the latent heat effect was not apparent mainly because the latent heat of solidification of cyclohexane is very low (approximately 1/13 of that corresponding to water). It may be noted that due to supercooling effects it is usually only the melting point, and not the solidification point, which can be compared with literature values.

Figure 9:
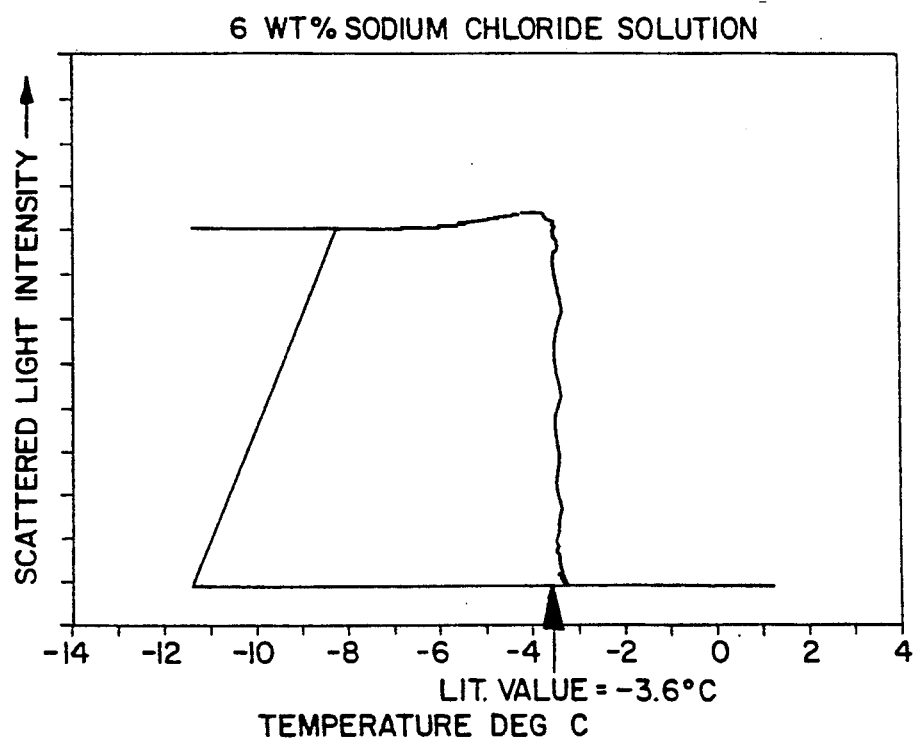

FIG. 9 shows the results for a 6% sodium chloride and water mixture. It can be seen that the melting point compares very well with the literature value.

Figure 10:
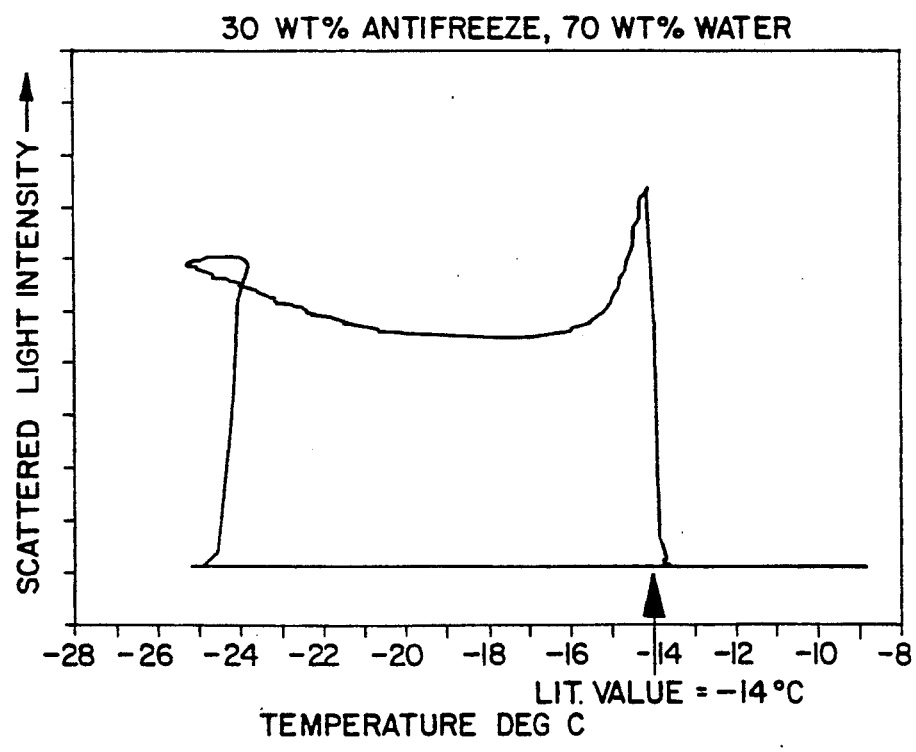

FIG. 10 shows the results for an ethylene glycol-water system. The freezing and melting temperatures were distinctly measured even though the mixtures were translucent rather than transparent. The measured values for melting point compared well with the literature value.

Figure 11:
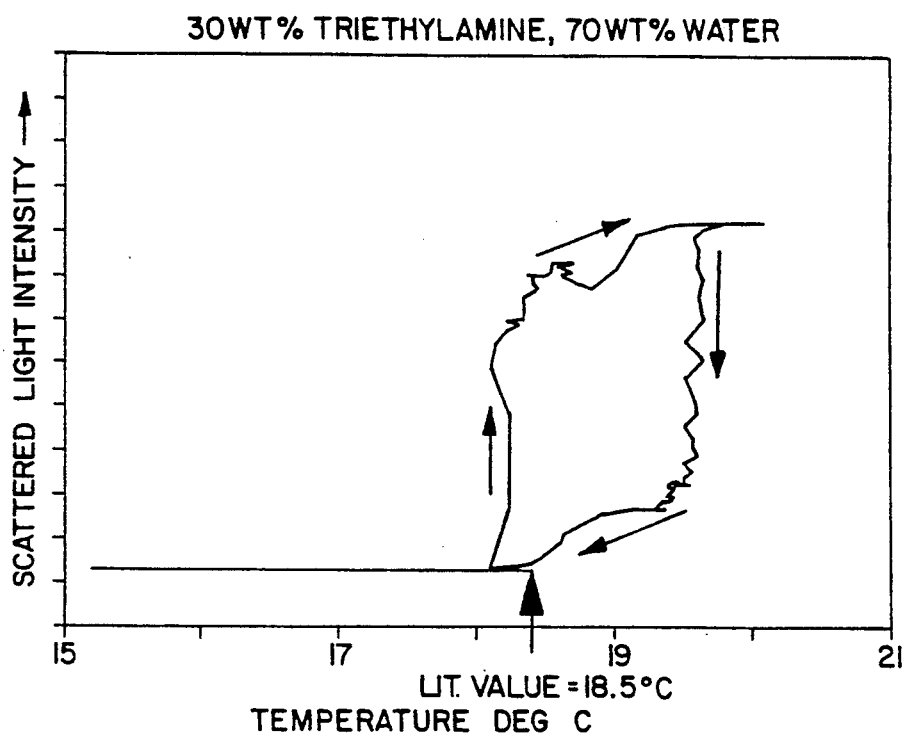

The detection of an immiscible liquid phase is shown in FIG. 11. This is a system with 30% triethylamine and 70% water. According to the literature, the system is completely miscible at temperatures below about 18.5° C. and becomes immiscible at temperatures higher than this level.

The experiment began at about 15° C. and the system was warmed up gradually. At about 18.1° C., the scattered light intensity increased significantly due to the separation of the two liquid phases. When the two phase system was cooled from 20° C., the two liquid phases became completely miscible again at about 18.1° C.

Figure 12:
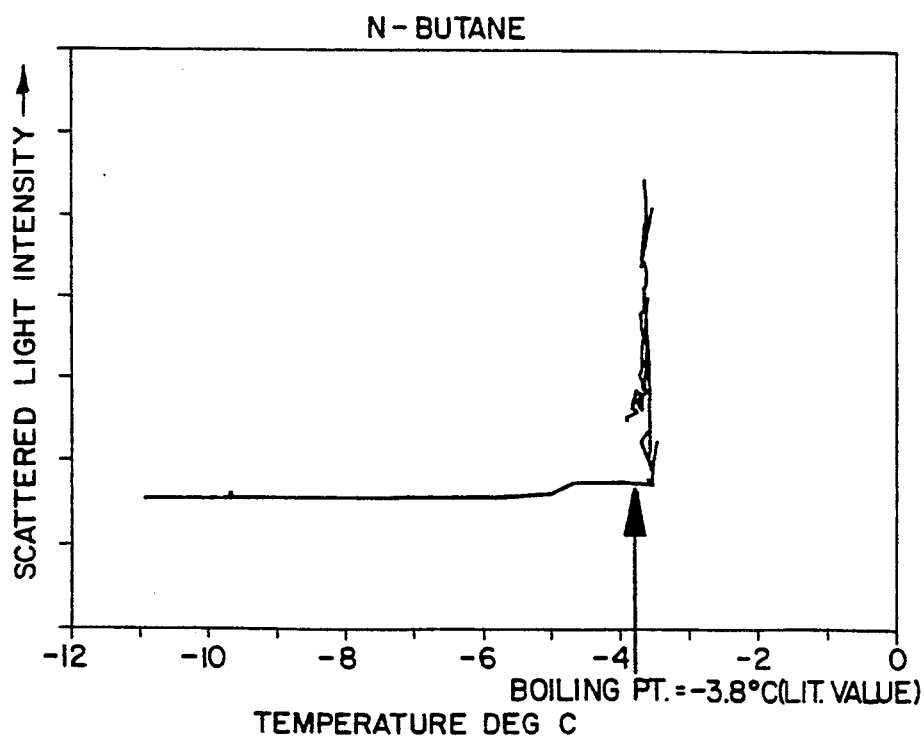

The results for a liquid-gas system are shown in FIG. 12. This shows the ability of this device to detect the boiling point of normal butane. The experiment began at about $-11°$ C., which was well below the boiling point of n-butane. As the temperature of the sample increased to $-3.7°$ C., the scattered light intensity rose substantially and then went up and down depending on the number and size of bubbles in the liquid phase. This behaviour continued until the entire sample was boiled off. It should be noted that in this experiment, the measurement cell was completely air-free; the vapour space of the cell was occupied by n-butane vapour.

We claim:

1. Apparatus for measuring the temperature at which a transition occurs in a material between a non-light scattering, transparent or translucent liquid phase and a light scattering phase, and capable of measuring cloud point, freezing point and melting point of a liquid, comprising;

a substantially light proof chamber having light-absorbing internal surfaces, gas purge inlet, said bottom temperature corresponding to the transition temperature of the sample when a change in scattered light is detected;

a light beam source located to direct a beam of light towards said upper surface at an incident angle of from 20° to 80° measured between the light beam and the surface so that light from the beam is largely reflected or absorbed by said upper surface; and scattered light detection means carried by said top part and arranged perpendicularly above said receptacle so as to detect light scattered by said sample and changes in intensity of the scattered light and connected into circuit means capable of registering change in light scattered from the said sample as said bottom is heated or cooled, said detection means including a lens which concentrates the light from the sample onto at least one light detecting element.

2. Apparatus according to claim 1 including a data processing and control means to control changing the temperature of said upper surface.

3. Apparatus according to claim 1 wherein said upper surface is a flat mirror surface.

4. Apparatus according to claim 1, wherein said cooling means is a thermoelectric cooler in thermal contact with said upper surface.

5. Apparatus according to claim 4, wherein said chamber is a housing having a bottom closure carrying said receptacle, and wherein said readily removable top part carries said light beam source as well as said light detection means, said light detection means including an array of light detecting elements.

6. Apparatus according to claim 5, wherein the main components of said closure, housing and top part are formed of plastic material, and wherein the cooling means is capable of reducing the temperature of the receptacle to less than $-50°$ C.

7. Apparatus according to claim 5, wherein the housing is annular and the top part is connected to the housing by a two component connecting means cmoprising radial pins projecting from one component arranged to fit within grooves in the other component.

8. Apparatus according to claim 5, wherein said array of light detecting elements is vertically movable relative to said lens for adjusting the focus of light received from the sample onto the array.

9. Apparatus according to claim 5, wherein said array of light detecting elements receives light from substantially the whole of area of said upper surface.

10. Apparatus according to claim 5, wherein said light beam source is a light-emitting diode mounted within the readily removable top part.

11. Apparatus according to claim 1, wherein said light beam source is a light-emitting diode mounted within said chamber.

12. Apparatus according to claim 1, wherein the receptacle has a transprent top which is removable for cleaning.

13. Apparatus according to claim 1, wherein said lens concentrates the light from the sample onto an array of light detecting elements.

14. Apparatus according to claim 13, wherein said array of light detecting elements is movable relative to the lens for adjusting the focus of light received from the sample onto the array.

15. Apparatus according to claim 1 including a data processing and control means to control changing the temperature of said upper surface.

16. Apparatus according to claim 1 wherein said upper surface is a flat mirror surface.

17. Apparatus according to claim 1, wherein the gas purge inlet means is connected to a source of dried gas.

18. Apparatus for measuring the temperature at which a transition occurs in a material between a transparent or translucent liquid phase and a light scattering phase, comprising:

a generally light proof chamber having lightabsorbing internal surfaces;

a liquid sample-receiving receptacle within said chamber having a bottom formed of a heat conductive material with an upper surface which is non-light scattering;

a removable, transparent top adapted to fit over the receptacle;

means allowing access to the chamber for placing a sample of the material in said receptacle and allowing removal of the material from the receptacle at the termination of the test;

means in thermal contact with said bottom for changing the temperature of said bottom and means for determining the temperature of said bottom in thermal contact therewith;

a light beam source located to direct a beam of light towards said surface at an incident angle so that light from the beam is largely reflected or absorbed by said surface; and scattered light detection means arranged so as to detect light scattered by said sample and changes in intensity of the scattered light and connected into circuit means capable of registering a change in light scattered from the said sample as said surface is heated or cooled.

* * * * *